United States Patent
Fabry et al.

[11] Patent Number: 5,981,450
[45] Date of Patent: *Nov. 9, 1999

[54] MILD DETERGENT MIXTURES

[75] Inventors: Bernd Fabry, Korschenbroich; Ansgar Behler, Bottrop, both of Germany

[73] Assignee: Henkel Kommanditgesellschaft auf Aktien, Duesseldorf, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/793,999

[22] PCT Filed: Sep. 7, 1995

[86] PCT No.: PCT/EP95/03505

§ 371 Date: Mar. 17, 1997

§ 102(e) Date: Mar. 17, 1997

[87] PCT Pub. No.: WO96/08551

PCT Pub. Date: Mar. 21, 1996

[30] Foreign Application Priority Data

Sep. 16, 1994 [DE] Germany ............... 44 33 071

[51] Int. Cl.$^6$ ............... C11D 1/02; C11D 1/20
[52] U.S. Cl. ............... 510/127; 510/135; 510/137; 510/138; 510/141; 510/156; 510/158; 510/159; 510/235; 510/340; 510/341; 510/350; 510/351; 510/427; 510/433; 510/488; 510/514; 510/536; 510/537; 510/490
[58] Field of Search ............... 510/127, 135, 510/137, 138, 141, 156, 158, 159, 235, 340, 341, 350, 351, 427, 433, 488, 514, 536, 537, 490

[56] References Cited

U.S. PATENT DOCUMENTS

| | | | |
|---|---|---|---|
| 4,554,097 | 11/1985 | Schebece et al. | 252/542 |
| 4,749,515 | 6/1988 | Miyamoto et al. | 252/545 |
| 5,071,960 | 12/1991 | Turowski et al. | 530/356 |
| 5,286,406 | 2/1994 | Scholz et al. | 252/174.17 |
| 5,296,158 | 3/1994 | MacGlip et al. | 252/108 |
| 5,308,526 | 5/1994 | Dias et al. | 252/125 |
| 5,312,559 | 5/1994 | Kacher et al. | 252/125 |
| 5,312,932 | 5/1994 | Behler et al. | 554/90 |
| 5,322,957 | 6/1994 | Fabry et al. | 558/23 |
| 5,458,881 | 10/1995 | Berger et al. | 424/401 |

FOREIGN PATENT DOCUMENTS

| | | |
|---|---|---|
| 0 417 619 | 3/1991 | European Pat. Off. |
| 936 632 | 8/1948 | France . |
| 1 459 789 | 2/1967 | France . |
| 1 466 141 | 4/1967 | France . |
| 1 500 775 | 1/1968 | France . |
| 36 37 683 | 5/1987 | Germany . |
| 42 03 490 A 1 | 8/1993 | Germany . |
| 44 10 000 | 3/1995 | Germany . |
| 01 288 267 | 11/1989 | Japan . |
| 1 170 092 | 11/1969 | United Kingdom . |
| WO91/14761 | 10/1991 | WIPO . |
| WO92/09569 | 6/1992 | WIPO . |
| WO92/09570 | 6/1992 | WIPO . |
| WO92/21318 | 12/1992 | WIPO . |

OTHER PUBLICATIONS

J. Am. Oil. Chem. Soc. 37, (1960) p. 171.
J. Oil Technol. Ass. Ind. (1972) p. 41.
J. Oil Technol. Ass. Ind. (1972) p. 41.
Indian J. Pharm. Sci. 41, (1979) p. 181.
J. Am. Oil. Chem. Soc., 49 (1972) p. 143.
Seifen Öle Fette Wachse, 108 (1982) p. 177.
Cosm. Toil., 99, (1984) p. 63.
Parf. Kosm. 72, (1991) p. 556.
Tens. Surf. Det. 29, (1992) p. 389.
Bull. Soc. Chim. Fr., (1950) p. 358.
Parf. Kosm. 45, (1964) p. 337.
J. Am. Oil Chem. Soc., 59, (1982) p. 217.
Surfactants in Consumer Products, J Falbe (ed.), Springer–Verlag, Berlin, 1987, pp. 54 to 124.
Katalysatoren, Tenside und Mineralöladditive, Thieme Verlag, Stuttgart, 1978 pp. 123 to 217.
"Kosmetische Färbemittel" der Farbstoffkommission der Deutschen Forschungsgemeinschaft, published by Verlag Chemie Weinheim, 1984, pp. 81 to 106.

*Primary Examiner*—Yogendra Gupta
*Assistant Examiner*—Gregory R. Delcotto
*Attorney, Agent, or Firm*—Ernest G. Szoke; Wayne C. Jaeschke; Real J. Grandmaison

[57] ABSTRACT

A surfactant mixture containing
(a) monoglyceride sulfates or monoglyceride ether sulfates, and
(b) amino acid derivatives selected from
(b1) acyl glutamates,
(b2) vegetable protein hydrolyzates, and
(b3) vegetable protein fatty acid condensates.

19 Claims, No Drawings

MILD DETERGENT MIXTURES

BACKGROUND OF THE INVENTION

1. Field of the Invention

This invention relates to detergent mixtures with improved dermal compatibility containing monoglyceride (ether) sulfates and selected amino acid derivatives, to surface-active formulations containing these mixtures and to the use of the mixtures for the production of surface-active formulations.

2. Discussion of Related Art

Formally, monoglyceride sulfates are products of the addition of sulfur trioxide to the primary hydroxyl group of a glycerol monofatty acid ester. Technically, however, they are complex anionic surfactant mixtures which are normally obtained by the simultaneous transesterification and sulfation of mixtures of triglycerides and glycerol and subsequent neutralization.

Monoglyceride sulfates are distinguished by satisfactory performance properties and good dermatological compatibility. Overviews on the production and properties of monoglyceride sulfates have been published, for example, by A. K. Biswas et al. in *J. Am. Oil. Chem. Soc.* 37, 171 (1960), R. Chamanial et al. in *J. Oil Technol. Ass. Ind.* 41 (1972) and J. K. Jain in *Indian J. Pharm. Sci.* 41, 181 (1979).

Detergent mixtures containing gelatin in addition to coconut monoglyceride sulfates are known from U.S. Pat. No. 4,554,097 (Colgate-Palmolive).

Unfortunately, the foaming behavior, especially in hard water, and dermatological compatibility of monoglyceride sulfates and the corresponding ether sulfates are not entirely satisfactory for a number of applications.

Accordingly, the problem addressed by the present invention was to find a way of significantly improving the performance and dermal compatibility of monoglyceride (ether) sulfates.

DESCRIPTION OF THE INVENTION

The present invention relates to mild detergent mixtures containing (a) monoglyceride (ether) sulfate s corresponding to formula (I):

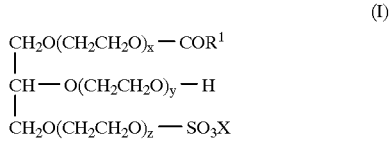

(I)

in which $R^1CO$ is a linear or branched acyl group containing 6 to 22 carbon atoms, x, y and z together are 0 or a number of 1 to 30 and X is an alkali metal or alkaline earth metal, and (b) amino acid derivatives selected from the group consisting of (b1) acyl glutamates corresponding to formula (II):

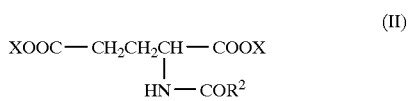

(II)

in which $R^2CO$ is a linear or branched acyl group containing 6 to 22 carbon atoms and 0 and/or 1, 2 or 3 double bonds and X is hydrogen, an alkali metal and/or alkaline earth metal, ammonium, alkylammonium, alkanolammonium or glucammonium, (b2) vegetable protein hydrolyzates and/or (b3) protein fatty acid condensates based on vegetable proteins and fatty acids containing 12 to 18 carbon atoms.

It has surprisingly been found that mixtures of monoglyceride sulfates or monoglyceride ether sulfates and the amino acid derivatives mentioned lead to synergistically improved dermal compatibility and increased foaming power.

Monoglycerides and monoglyceride ether sulfates

Monoglyceride sulfates and monoglyceride ether sulfates are known anionic surfactants which may be obtained by the relevant methods of preparative organic chemistry. They are normally produced from triglycerides which are transesterified to the monoglycerides, optionally after ethoxylation, and subsequently sulfated and neutralized. The partial glycerides may also be reacted with suitable sulfating agents, preferably gaseous sulfur trioxide or chlorosulfonic acid [cf. WO 92/09569, WO 92/09570, Henkel KGaA]. If desired, the neutralized substances may be subjected to ultrafiltration to reduce the electrolyte content to the required level.

Typical examples of monoglyceride (ether) sulfates suitable for use in accordance with the invention are the reaction products of lauric acid monoglyceride, cocofatty acid monoglyceride, palmitic acid monoglyceride, stearic acid monoglyceride, oleic acid monoglyceride and tallow fatty acid monoglyceride and ethylene oxide adducts thereof with sulfur trioxide or chlorosulfonic acid in the form of the sodium salts. Monoglyceride sulfates corresponding to formula (I), in which $R^1CO$ is a linear acyl group containing 8 to 18 carbon atoms, are preferably used.

Acyl glutamates

Acyl glutamates are known anionic surfactants. They are produced, for example, by Schotten-Baumann acylation of glutamic acid with fatty acids, fatty acid esters or chlorides. Commercial products are available, for example, from Hoechst AG, Frankfurt, DE or from the Ajinomoto Co. Inc., Tokyo, JP. A review of the production and properties of acyl glutamates was published by M. Takehara et al. in *J. Am Oil. Chem. Soc.* 49, 143 (1972).

Formally, glutamic acid is one of the products which would be obtained in the total hydrolysis of proteins. In fact, however, the hydrolysis of proteins leads to mixtures of oligopeptides which still contain an average of 5 to 20 amino acid units. Accordingly, protein fatty acid condensates are normally acylation products of oligopeptides. Acyl glutamates differ from these substances in that, in a way, they represent "monomers".

Typical examples of acyl glutamates suitable for the purposes of the invention are anionic surfactants derived from fatty acids containing 6 to 22 and preferably 12 to 18 carbon atoms, for example $C_{12/14}$ or $C_{2/8}$ cocofatty acid, lauric acid, myristic acid, palmitic acid and/or stearic acid. Sodium-N-cocoyl glutamate and sodium-N-stearoyl-L-glutamate are particularly preferred.

Vegetable protein hydrolyzates

Vegetable protein hydrolyzates are degradation products of, for example, pea, potato, rice, almond and—preferably—soya or wheat proteins which are split by acidic, alkaline and/or enzymatic hydrolysis and, thereafter, have an average molecular weight of 600 to 4,000 and preferably 2,000 to 3,500. Although protein hydrolyzates are not surfactants in the accepted sense through the absence of a hydrophobic component, they are often used for formulating surface-active products by virtue of their dispersing properties. Reviews of the production and use of protein hydrolyzates have been published, for example, by G. Schuster and A. Domsch in *Seifen Öle Fette Wachse* 108, 177 (1982) and *Cosm. Toil.* 99, 63 (1984), by H. W. Steisslinger in *Parf. Kosm.* 72, 556 (1991) and by F. Aurich et al. in *Tens. Surf. Det.* 29, 389 (1992).

Protein fatty acid condensates

Protein fatty acid condensates are known substances which are preferably produced from the vegetable hydrolyzates mentioned above by Schotten-Baumann acylation, preferably using fatty acid chlorides. Overviews of this subject have been published, for example, by M. Naudet in *Bull. Soc. Chim. Fr.*, 358 (1950), by G. Schuster et al. in *Parf. Kosm.* 45, 337 (1964) and by O.J. Muscio et al. in *J. Am. Oil. Chem. Soc.* 59, 217 (1982).

Formally, the protein hydrolyzates to be used in accordance with the invention are products of the acylation of—preferably—wheat or soya protein hydrolyzates with aliphatic fatty acids corresponding to formula (III):

$$R^3CO\text{---}OH \quad (III)$$

in which $R^3CO$ is an aliphatic acyl group containing 6 to 22 and preferably 12 to 18 carbon atoms. As already described, however, the fatty acyl group is introduced into the condensates through the fatty acid chlorides and not through the fatty acids. Accordingly, any mention in the following of the fatty acids from which the protein fatty acid condensates are derived is linked with the teaching that the corresponding fatty acid chlorides should be used for their production.

Examples of fatty acids from which the protein fatty acid condensates may formally be derived are caproic acid, caprylic acid, 2-ethyl hexanoic acid, isononanoic acid, capric acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtainable, for example, by pressure hydrolysis of fats and oils, or reduction of aldehydes from Roelen's oxosynthesis.

The protein fatty acid condensates may be used in the form of their alkali metal, alkaline earth metal and/or ammonium salts, preferably in the form of their sodium, potassium, magnesium and/or calcium salts. Protein fatty acid condensates based on wheat and/or soya protein or hydrolyzates thereof and fatty acids containing 12 to 18 carbon atoms are preferably used. Highly acylated protein fatty acid condensates with a total nitrogen content of 1.8 to 4.1 and preferably 2.5 to 3.5 are also preferred.

Surfactants

The detergent mixtures according to the invention may contain other anionic, nonionic, cationic and/or amphoteric surfactants.

Typical examples of anionic surfactants are alkyl benzene sulfonates, alkane sulfonates, olefin sulfonates, alkyl ether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, fatty acid amide (ether) sulfates, mono- and dialkyl sulfosuccinates, mono- and dialkyl sulfosuccinamates, sulfotriglycerides, amide soaps, alkyl oligoglucoside sulfates and alkyl (ether) phosphates. If the anionic surfactants contain polyglycol ether chains, they may have a conventional homolog distribution although they preferably have a narrow homolog distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides and fatty acid N-alkyl glucamides. If the nonionic surfactants contain polyglycol ether chains, they may have a conventional homolog distribution although they preferably have a narrow homolog distribution.

Typical examples of cationic surfactants are quaternary ammonium compounds and esterquats, more particularly quaternized fatty acid trialkanolamine ester salts.

Typical examples of amphoteric or zwitterionic surfactants are alkyl betaines, alkyl amidobetaines, aminopropionates, aminoglycinates, imidazolinium betaines and sulfobetaines.

All the surfactants mentioned are known compounds. Information on their structure and production can be found in relevant synoptic works, cf. for example J. Falbe (ed.), (*Surfactants in Consumer Products*", Springer Verlag, Berlin, 1987, pages 54 to 124 or J. Falbe (ed.), "*Katalysatoren, Tenside und Mineralöladditive*", Thieme Verlag, Stuttgart, 1978, pages 123–217.

The detergent mixtures according to the invention may contain the additional surfactants mentioned above in quantities of 1 to 50% by weight and preferably in quantities of 5 to 25% by weight, based on the solids content of the mixtures.

COMMERCIAL APPLICATIONS

The detergent mixtures according to the invention are distinguished by particularly advantageous foaming power and by synergistically improved dermal compatibility—properties which are important in the development of a number of surface-active formulations.

Accordingly, the present invention also relates to surface-active formulations containing these detergent mixtures which are defined in more detail in the following:

Powder-form heavy-duty detergents containing 10 to 30% by weight, based on the detergent, of the detergent mixtures according to the invention and typical auxiliaries and additives.

Liquid heavy-duty detergents containing 10 to 70% by weight, based on the detergent, of the detergent mixtures according to the invention and typical auxiliaries and additives.

Liquid light-duty detergents containing 10 to 50% by weight, based on the detergent, of the detergent mixtures according to the invention and typical auxiliaries and additives.

Fabric softeners containing 10 to 50% by weight, based on the softener, of the detergent mixtures according to the invention and typical auxiliaries and additives.

Manual dishwashing detergents containing 10 to 50% by weight, based on the detergent, of the detergent mixtures according to the invention and typical auxiliaries and additives.

Rinse aids containing 10 to 50% by weight, based on the rinse aid, of the detergent mixtures according to the invention and typical auxiliaries and additives.

Liquid cleaners and disinfectants containing 10 to 30% by weight, based on the cleaner/disinfectant, of the detergent mixtures according to the invention and typical auxiliaries and additives.

Bar soaps of the combination bar type containing 1 to 2% by weight, based on the bar soap, of the detergent mixtures according to the invention and typical auxiliaries and additives.

Syndet soaps containing 1 to 2% by weight, based on the syndet soap, of the detergent mixtures according to the invention and typical auxiliaries and additives.

Hair shampoos containing 10 to 30% by weight, based on the shampoo, of the detergent mixtures according to the invention and typical auxiliaries and additives.

Hair rinses containing 10 to 30% by weight, based on the hair rinse, of the detergent mixtures according to the invention and typical auxiliaries and additives.

Hair colorants containing 10 to 30% by weight, based on the colorant, of the detergent mixtures according to the invention and typical auxiliaries and additives.

Hair wave sets containing 10 to 30% by weight, based on the wave set, of the detergent mixtures according to the invention and typical auxiliaries and additives.

Foam baths containing 10 to 30% by weight, based on the foam bath, of the detergent mixtures according to the invention and typical auxiliaries and additives.

Textile and fiber auxiliaries containing 1 to 30% by weight, based on the auxiliary, of the detergent mixtures according to the invention and typical auxiliaries and additives.

Leather oiling formulations containing 1 to 30% by weight, based on the oiling formulation, of the detergent mixtures according to the invention and typical auxiliaries and additives.

Flotation aids containing 1 to 30% by weight, based on the flotation aid, of the detergent mixtures according to the invention and typical auxiliaries and additives.

Auxiliaries for the dewatering of solids containing 1 to 30% by weight, based on the auxiliary, of the detergent mixtures according to the invention and typical auxiliaries and additives.

Auxiliaries and additives

Laundry detergents, dishwashing detergents, cleaners and fabric softeners based on the detergent mixtures according to the invention may contain, for example, builders, salts, bleaching agents, bleach activators, optical brighteners, redeposition inhibitors, solubilizers and enzymes as further auxiliaries and additives in addition to the surfactants already mentioned.

Typical builders are sodium aluminium silicates (zeolites), phosphates, phosphonates, ethylenediamine tetraacetic acid, nitrilotriacetate, citric acid and/or polycarboxylates.

Suitable salts and extenders are, for example, sodium sulfate, sodium carbonate or sodium silicate (waterglass). Typical individual examples of other additives are sodium borate, starch, sucrose, polydextrose, TAED, stilbene compounds, methyl cellulose, toluene sulfonate, cumene sulfonate, long-chain soaps, silicones, mixed ethers, lipases and proteases.

Hair shampoos, hair lotions or foam baths may contain emulsifiers, such as alkoxylated fatty alcohols or sorbitan esters for example, as further auxiliaries and additives in addition to the surfactants already mentioned.

Suitable superfatting agents are such substances as, for example, polyethoxylated lanolin derivatives, lecithin derivatives and fatty acid alkanolamides, the fatty acid alkanolamides also serving as foam stabilizers.

Suitable thickeners are, for example, polysaccharides, more particularly xanthan gum, guar guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride.

Suitable biogenic agents are, for example, plant extracts and vitamin complexes.

Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives and similar compounds.

Suitable preservatives are, for example, phenoxyethanol, formaldehyde solution, parabens, pentanediol or sorbic acid.

Suitable pearlescers are, for example, glycol distearic acid esters, such as ethylene glycol distearate, and fatty acid monoglycol esters.

The dyes used may be any of the substances suitable and licensed for cosmetic purposes, as listed for example in the publication entitled *"Kosmetische Färbemittel" der Farbstoffkommission der Deutschen Forschungsgemeinschaft*, published by Verlag Chemie, Weinheim, 1984, pages 81–106. These dyes are normally used in concentrations of 0.001 to 0.1% by weight, based on the mixture as a whole.

The total content of auxiliaries and additives may be 1 to 50% by weight and is preferably 5 to 40% by weight, based on the particular formulation.

The detergent mixtures according to the invention are suitable for the production of liquid or solid surface-active formulations in which they may be present in quantities of 1 to 99% by weight and preferably 10 to 90% by weight, based on the solids content of the formulation.

EXAMPLES

I. Surfactants used

A1) $C_{12/18}$ coconut monoglyceride sulfate sodium salt

B1) N-lauryl glutamate sodium salt

B2) Wheat protein hydrolyzate containing on average 7 peptide units

B3) Wheat protein/coconut fatty acid condensate potassium salt

II. Results of performance tests

Foaming power was determined in accordance with DIN 53902, Part 2 (Ross Miles Test) using 1% by weight surfactant solutions in water with a hardness of 16° d. The temperature was 20° C. The basic foam and foam volume after 5 minutes were determined.

The irritation potential was determined by OECD Method No. 404 and in accordance with EEC Directive 84/449 EEC, Pt.B.4. The total irritation scores shown were formed from the irritation scores obtained after 24, 48 and 72 hours. The total irritation score for a 100% $C_{12/18}$ coconut fatty acid monoglyceride sulfate sodium salt determined in comparison test C1 was put at 100% and the total irritation scores obtained in the other tests were related to that score.

The results are set out in Table 1 (percentages as % by weight).

TABLE 1

Foaming Power and Irritation Potential

| Ex. | [A1] | B | [B] | Foam Height [ml] Immediately | After 5 mins. | Total Irritation Score %-Rel |
|---|---|---|---|---|---|---|
| 1 | 50 | B1 | 50 | 560 | 430 | 52 |
| 2 | 70 | B1 | 30 | 590 | 450 | 55 |
| 3 | 70 | B2 | 30 | 490 | 320 | 45 |
| 4 | 70 | B3 | 30 | 570 | 420 | 57 |
| C1 | 100 | — | — | 500 | 300 | 100 |

TABLE 1-continued

Foaming Power and Irritation Potential

| Ex. | [A1] | B | [B] | Foam Height [ml] Immediately | After 5 mins. | Total Irritation Score %-Rel |
|---|---|---|---|---|---|---|
| C2 | 0 | B1 | 100 | 450 | 310 | 65 |
| C3 | 0 | B2 | 100 | 50 | 0 | 55 |
| C4 | 0 | B3 | 100 | 400 | 250 | 70 |

What is claimed is:

1. A surfactant mixture consisting essentially of
   (a) monoglyceride sulfates or monoglyceride ether sulfates, and
   (b) amino acid derivatives selected from the group consisting of wheat—or soya—derived vegetable protein hydrolyzates having an average molecular weight of 600 to 4000, and wheat—or soya—derived vegetable protein fatty acid condensates wherein the weight ratio of sulfates to amino acid derivatives is 1:99 to 99:1.

2. A surfactant mixture according to claim 1 wherein said monoglyceride sulfates or monoglyceride ether sulfates correspond to formula (I)

$$\begin{array}{l} CH_2O(CH_2CH_2O)_x-COR^1 \\ | \\ CH-O(CH_2CH_2O)_y-H \\ | \\ CH_2O(CH_2CH_2O)_z-SO_3X \end{array} \quad (I)$$

in which $R^1CO$ is a linear or branched acyl group containing 6 to 22 carbon atoms, x, y and z together are 0 or a number of 1 to 30 and X is an alkali metal or alkaline earth metal.

3. A surfactant mixture according to claim 1 wherein said vegetable protein fatty acid condensates are derived from vegetable proteins and fatty acids containing 12 to 18 carbon atoms.

4. A surfactant mixture according to claim 1 present in a detergent composition in an amount of 10% to 70% by weight, based on the weight of said detergent composition.

5. A surfactant mixture according to claim 4 wherein said detergent composition is a granular, heavy-duty detergent composition.

6. A surfactant mixture according to claim 4 wherein said detergent composition is a liquid, heavy-duty detergent composition.

7. A surfactant mixture according to claim 4 wherein said detergent composition is a liquid, light-duty detergent composition.

8. A surfactant mixture according to claim 4 wherein said detergent composition is a manual dishwashing detergent composition.

9. A surfactant mixture according to claim 1 present in a rinse aid composition in an amount of 10% to 50% by weight, based on the weight of said rinse aid composition.

10. A surfactant mixture according to claim 1 present in a liquid cleaner/disinfectant composition in an amount of 10% to 30% by weight, based on the weight of said liquid cleaner/disinfectant composition.

11. A surfactant mixture according to claim 1 present in a bar soap in an amount of 1% to 2% by weight, based on the weight of said bar soap.

12. A surfactant mixture according to claim 1 present in a hair shampoo composition in an amount of 10% to 30% by weight, based on the weight of said hair shampoo composition.

13. A surfactant mixture according to claim 1 present in a hair rinse composition in an amount of 10% to 30% by weight, based on the weight of said hair rinse composition.

14. A surfactant mixture according to claim 1 present in a hair colorant composition in an amount of 10% to 30% by weight, based on the weight of said hair colorant composition.

15. A surfactant mixture according to claim 1 present in a hair wave set composition in an amount of 10% to 30% by weight, based on the weight of said hair wave set composition.

16. A surfactant mixture according to claim 1 present in a bubble bath composition in an amount of 10% to 30% by weight, based on the weight of said bubble bath composition.

17. A surfactant mixture according to claim 1 present in a textile treating composition in an amount of 1% to 30% by weight, based on the weight of said textile treating composition.

18. A surfactant mixture according to claim 1 present in a leather oiling composition in an amount of 1% to 30% by weight, based on the weight of said leather oiling composition.

19. A surfactant mixture according to claim 1 present in a flotation aid composition in an amount of 1% to 30% by weight based on the weight of said flotation aid composition.

* * * * *